(12) United States Patent
Tsubouchi et al.

(10) Patent No.: US 7,311,923 B2
(45) Date of Patent: Dec. 25, 2007

(54) HARMFUL-INSECT-ELIMINATING FORMED RESIN ARTICLE AND ANIMAL COLLAR USING THE SAME

(75) Inventors: Kaori Tsubouchi, Ibaraki (JP); Kenzo Hayama, Nagaokakyo (JP)

(73) Assignee: Sumitomo Chemical Company, Limited, Osaka (JP)

( * ) Notice: Subject to any disclaimer, the term of this patent is extended or adjusted under 35 U.S.C. 154(b) by 265 days.

(21) Appl. No.: 10/379,691

(22) Filed: Mar. 6, 2003

(65) Prior Publication Data

US 2004/0028715 A1    Feb. 12, 2004

(30) Foreign Application Priority Data

Mar. 11, 2002    (JP)    ............................. 2002-066073

(51) Int. Cl.
*A01N 25/10*    (2006.01)

(52) U.S. Cl. ...................... 424/411; 424/405; 424/406; 514/454; 514/690

(58) Field of Classification Search ................ 424/409, 424/111, 742; 514/675, 693, 724, 919
See application file for complete search history.

(56) References Cited

U.S. PATENT DOCUMENTS

| 4,150,109 | A | * | 4/1979 | Dick et al. | ................... 424/411 |
| 5,856,271 | A | * | 1/1999 | Cataldo et al. | .............. 504/360 |
| 5,885,600 | A | * | 3/1999 | Blum et al. | .................. 424/405 |
| 6,329,433 | B1 | * | 12/2001 | Bessette et al. | ............. 514/729 |

\* cited by examiner

*Primary Examiner*—Neil S. Levy
(74) *Attorney, Agent, or Firm*—Sughrue Mion, PLLC

(57) ABSTRACT

Disclosed is a harmful-insect-eliminating formed resin article, wherein the article contains a 1,2-polybutadiene resin and a volatile harmful-insect-eliminating component, e.g. eucalyptol and pulegone, in an amount effective for eliminating a harmful insect. A typical use of the formed article is an animal collar.

9 Claims, No Drawings

HARMFUL-INSECT-ELIMINATING FORMED RESIN ARTICLE AND ANIMAL COLLAR USING THE SAME

BACKGROUND OF THE INVENTION

1. Field of the Invention

The present invention relates to a harmful-insect-eliminating formed resin article containing a volatile harmful-insect-eliminating component and to an animal collar using the harmful-insect-eliminating formed resin article.

2. Description of the Related Art

Formed resin articles containing volatile harmful-insect-eliminating components are widely used for the purpose of harmful insect elimination. For example, animal collars comprising such formed resin articles are known. The formed resin articles containing volatile harmful-insect-eliminating components are used widely in various fields since the formed articles can release the harmful-insect-eliminating components slowly from surfaces thereof through volatilization of the volatile harmful-insect-eliminating components and/or bleeding of the components to the surfaces of the articles and therefore can exhibit an efficacy in eliminating harmful insects for a long period of time.

In many harmful-insect-eliminating formed resin articles, polyvinyl chloride resins are used as a base resin. However, from the considerations for the environment, use of chlorine atom-free resins in place of polyvinyl chloride resins has recently been desired in the field of formed articles for consumer use such as animal collars.

To solve the above-mentioned problems, harmful-insect-eliminating formed resin articles containing an ethylene-vinyl acetate copolymer, which is a polyolefin resin having a polar group, have conventionally been used and animal collars comprising such harmful-insect-eliminating formed resin articles have been marketed.

However, a harmful-insect-eliminating formed resin article using a polyolefin resin having a polar group such as an ethylene-vinyl acetate copolymer as a base resin may inferior in practical utilities to formed articles using a polyvinyl chloride resin as a base resin. Specifically, a harmful-insect-eliminating formed resin article using a polyolefin resin having a polar group is harder than that containing a polyvinyl chloride resin as a base resin. Therefore, the harmful-insect-eliminating formed resin article using a polyolefin resin having a polar group is difficult to be used for applications where flexibility is required, such as animal collars. Furthermore, in a harmful-insect-eliminating formed resin article using an ethylene-vinyl acetate copolymer as a base resin, the volatilization rate of the volatile harmful-insect-eliminating component contained is great and therefore an efficacy in eliminating harmful insects can not be held over a long period of time.

SUMMARY OF THE INVENTION

The present invention was made by taking the above-mentioned problems into consideration. The object of the present invention is to provide a harmful-insect-eliminating formed resin article and an animal collar, those items being capable of continuing to exhibit an efficacy in eliminating harmful insects for a long period of time.

To solve the above-mentioned problem, the harmful-insect-eliminating formed resin article of the present invention is characterized by containing a 1,2-polybutadiene resin and a volatile harmful-insect-eliminating component in an amount effective for eliminating a harmful insect.

This harmful-insect-eliminating formed resin article contains a 1,2-polybutadiene resin as a base resin. It therefore can have a flexibility the same as that of conventional harmful-insect-eliminating formed resin articles containing a polyvinyl chloride resin as a base resin. In addition, since the 1,2-polybutadiene resin gives less bad effect to the environment than polyvinyl chloride resins do, the harmful-insect-eliminating formed resin article of the present invention can be used preferably. Furthermore, since the harmful-insect-eliminating formed resin article of the present invention contains a 1,2-polybutadiene resin as a base resin, the volatilization of the volatile harmful insect eliminating component is controlled more effectively in comparison with formed articles containing a polyolefin resin having a polar group as a base resin, and it can exhibit an efficacy in eliminating harmful insects for a long period of time. Accordingly, the harmful-insect-eliminating formed resin article of the present invention can be used for applications such as animal collars.

In the harmful-insect-eliminating formed resin article of the present invention, it is more preferable that the volatile harmful-insect-eliminating component is at least one substance selected from eucalyptol and pulegone.

This harmful-insect-eliminating formed resin article contains a 1,2-polybutadiene resin as a base resin and also contains at least one substance selected from eucalyptol and pulegone as a volatile harmful-insect-eliminating component. It therefore can exhibit an efficacy in eliminating harmful insects for a long period of time.

In the harmful-insect-eliminating formed resin article of the present invention, it is more preferable that the 1,2-polybutadiene resin comprise 1,2-polybutadiene containing monomer units polymerized through a 1,2-addition reaction in an amount of not less than 90% of the whole monomer units constituting the 1,2-polybutadiene resin.

In the harmful-insect-eliminating formed resin article of the present invention, it is more preferable that the monomer units form a syndiotactic structure.

It is more preferable that the harmful-insect-eliminating formed resin article of the present invention have a hardness, as measured with a type A durometer according to JIS K6253, within the range of from 60 to 77.

The animal collar of the present invention is characterized by comprising any of the above-mentioned harmful-insect-eliminating formed resin articles.

Since the animal collar of the above constitution comprises a harmful-insect-eliminating formed resin article containing a 1,2-polybutadiene resin and a volatile harmful-insect-eliminating component, it is superior in flexibility, and can exhibit an efficacy in eliminating harmful insects for a long period of time.

DESCRIPTION OF PREFERRED EMBODIMENTS

Some embodiments of the present invention are described below, but the invention is not restricted thereto.

The harmful-insect-eliminating formed resin article of the present invention contains a 1,2-polybutadiene resin and a volatile harmful-insect-eliminating component.

The harmful-insect-eliminating formed resin article of the present invention contains a 1,2-polybutadiene resin as a base resin. It is preferable that monomer units polymerized through a 1,2-addition reaction are contained in an amount of not less than 90% of the whole monomer units constituting the 1,2-polybutadiene resin. When the monomer units polymerized through a 1,2-addition reaction are less than 90%, the volatilization of the volatile harmful-insect-eliminating component may become slow, resulting in an insufficient harmful-insect-eliminating effect.

The tacticity of the 1,2-polybutadiene resin may be atactic, syndiotactic or isotactic, and is preferably syndiotactic. When the tacticity of the 1,2-polybutadiene is syndiotactic, it becomes easy to control the volatilization of the volatile harmful-insect-eliminating component. In such an event, an efficacy in eliminating harmful insects is fully exhibited and the efficacy can be held for a long time.

Accordingly, with respect to the base resin of the harmful-insect-eliminating formed resin article of the present invention, the 1,2-polybutadiene resin is preferably syndiotactic 1,2-polybutadiene containing monomer units polymerized through a 1,2-addition reaction in an amount of not less than 90% of the whole monomer units constituting the 1,2-polybutadiene resin.

In the base resin of the harmful-insect-eliminating formed article of the present invention, one or more kinds of resin other than 1,2-polybutadiene (henceforth, referred to as "other resin") maybe contained unless the desired effect of the present invention is damaged greatly.

Specific examples of the "other resin" include resins, for example, polyolefin resins such as polyethylene resins, e.g. high density polyethylene, low density polyethylene, linear low density polyethylene, ultra low density polyethylene and copolymers of ethylene and an a-olefin having three or more carbon atoms, propylene homopolymers, random or block copolymers of propylene and an α-olefin having four or more carbon atoms, copolymers of ethylene and carboxylic acid derivative(s) having an ethylenic unsaturated bond, e.g. ethylene-methyl methacrylate copolymers, ethylene-vinyl acetate copolymers, ethylene-acrylic acid copolymers and ethylene-vinyl acetate-methyl methacrylate copolymers, polyvinyl alcohol and polyvinyl acetate; rubbers, for example, 1,4-polybutadiene, polyisoprene and styrene-butadiene copolymers; polymers comprising cyclic olefins and hydrogenated products thereof; petroleum resins; rosin resins; chroman-indene resins; and terpene resins. The "other resin" may be chosen appropriately depending upon the kind of the volatile harmful-insect-eliminating component used and the application of the harmful-insect-eliminating formed resin article.

The blending ratio of the 1,2-polybutadiene resin and the other resin is not particularly restricted unless the desired effect of the present invention is damaged greatly. However, for exhibiting the effect resulting from the blending of the 1,2-polybutadiene resin, it is preferable to blend them so that the 1,2-polybutadiene resin accounts for not less than 70% by weight, more preferably not less than 90% by weight, of the whole base resin.

When the amount of the 1,2-polybutadiene resin is let be not less than 70% by weight, more preferably not less than 90% by weight, of the whole base resin, a harmful-insect-eliminating formed resin article excellent in flexibility can be provided.

The volatile harmful-insect-eliminating component is not particularly restricted as long as it has both volatility and an efficacy in eliminating harmful insects.

In the present invention, the volatile harmful-insect-eliminating component means both a component having volatility and an efficacy in killing harmful insects and a component having volatility and an efficacy in repelling harmful insects.

A component having volatility means a component having a saturation vapor pressure of not lower than $1 \times 10^{-6}$ mmHg (that is, not lower than 0.13 Pa) at 20° C., preferably a saturation vapor pressure of not lower than $1 \times 10^{-5}$ mmHg and not higher than $1 \times 10^{-2}$ mmHg (that is, not lower than 1.33 Pa and not higher than 1330 Pa) at 20° C.

Examples of the volatile harmful-insect-eliminating component include synthetic pyrethroids, organophosphorus compounds, and carbamate compounds.

Specific examples of the synthetic pyrethroid compounds include allethrin and empenthrin.

Specific examples of the organophosphorus compounds include fenthion, cyanophos and diazinon.

Examples of the carbamate compounds include methoxadiazon.

Examples of other volatile harmful-insect-eliminating components include eucalyptol, pulegone, cypress pure oil, natural pyrethrin.

The harmful-insect-eliminating formed resin article of the present invention contains at least one kind of harmful-insect-eliminating component and it may contain two or more kinds of harmful-insect-eliminating components depending upon a desired effect. For example, when harmful-insect-eliminating components differing in volatilization rate are contained in combination in a harmful-insect-eliminating formed article, an efficacy in eliminating a harmful insect for a longer period of time. On the other hand, when harmful-insect-eliminating components differing in the kind of insect to be eliminated are contained in combination in a harmful-insect-eliminating formed article, it is possible to eliminate a plurality of kinds of insects.

Of the above-listed volatile harmful-insect-eliminating components, particularly preferred are eucalyptol and/or pulegone. When eucalyptol and/or pulegone are/is combined with 1,2-polybutadiene to form a harmful-insect-eliminating formed resin article, the formed article can be produced easily and an efficacy in eliminating harmful insects such as flea can be exhibited for a long period of time.

The harmful-insect-eliminating formed resin article of the present invention contains a volatile harmful-insect-eliminating component in an amount effective for eliminating a harmful insect, that is, in an amount sufficient to exhibit an efficacy in eliminating harmful insects. A preferable amount of that component varies depending, for example, upon the kind of the component and the application of the formed article. The amount of harmful-insect-eliminating component in the harmful-insect-eliminating formed resin article decreases with time as the volatilization of the component proceeds. However, the preferable amount is within the range of from 0.5 to 30% by weight, more preferably within the range of from 0.5 to 15% by weight, based on the weight of the base resin. When the amount of the harmful-insect-eliminating component is brought within the above-mentioned ranges, it is easy to produce a harmful-insect-eliminating formed resin article capable of exhibiting an efficacy in eliminating harmful insects for a long period of time.

The hardness of the harmful-insect-eliminating formed resin article of the present invention is preferably within the range of from 60 to 77, more preferably within the range of from 65 to 75. If the hardness is lower than 60 or if it is greater than 77, the formed article may be unsuitable for some applications. Therefore, when the hardness is brought within the range of from 60 to 77, the harmful-insect-eliminating formed resin article is superior in flexibility and excellent in practical utility.

The hardness is a value measured with a type A durometer according to JIS K6253.

The harmful-insect-eliminating formed resin article of the present invention may contain components other than the base resin and the volatile harmful-insect-eliminating component, such as fillers, antioxidants and pigments, as required.

The method for blending the volatile harmful-insect-eliminating component to the base resin is not particularly restricted. Specifically, for example, a pellet-formed resin composition can be produced by mixing of raw materials with a mixing device such as a Banbury mixer and an extruder, followed by pelletization. It is also possible to obtain a powdery resin composition by mixing the volatile harmful-insect-eliminating component to powdery 1,2-polybutadiene resin with a supermixer or the like. The method for powdering 1,2-polybutadiene resin also is not particularly restricted. For example, freeze grinding can be employed.

The harmful-insect-eliminating formed resin article of the present invention can easily be produced by a known forming method, e.g. injection molding, extrusion forming, press forming and slush molding. Depending upon purposes such as improvement of dynamic properties at the time of use of the formed article, increase of the concentration of a volatile harmful-insect-eliminating component in the surface of the formed article and improvement of processability and formability, a composite formed article may be produced by various methods conventionally known, e.g. multilayer extrusion forming, multi-color injection molding, composite spinning and extrusion lamination.

The harmful-insect-eliminating formed resin article of the present invention can be used, for example, for animal collars, animal ear tags and animal medals. Moreover, depending upon applications and modes of use, the formed article can be used by being processed into various shapes such as a solid body, a planar body and a rod or by being fabricated into various items such as nets, fibers, non-woven fabrics, sheets and films.

In addition, the animal collar of the present invention uses a harmful-insect-eliminating formed resin article. Accordingly, the harmful-insect-eliminating formed resin article is used in the whole or part of the animal collar. The shape of the animal collar varies depending, for example, upon the kind of animal which is to wear the collar. However, those sized 20-60 cm in length, 0.8-1.5 cm in width, and 0.2-0.5 cm in thickness are used suitably.

EXAMPLES

Example 1

To 48.05 g of 1,2-polybutadiene (available as RB810 from JSR) melt kneaded with a plastograph (circulating oil temperature 140° C.) equipped with a stirrer, a mixed liquid of 0.35 g of eucalyptol and 1.6 g of pulegone was dropped and the mixture was stirred for one minute, resulting in a resin composition. The resin composition was press formed at 140° C. to yield a sheet (harmful-insect-eliminating formed resin article) which was 7.5 cm long, 5.5 cm wide and 3 mm thick.

The residual ratios of the harmful-insect-eliminating components contained in the harmful-insect-eliminating formed resin article were determined by the method described below.

(Measurement of Hardness of Formed Resin Article)

The hardness of a formed resin article was measured with a type A durometer according to JIS K6253. In the measurement, two pieces of sheet 3 mm in thickness were used in pile. After both sheets were brought in tight contact by application of force, the hardness after 0.5 second was measured. The results are shown in Table 1.

(Measurement of Residual Ratio of Harmful-insect-eliminating Component)

About 1 g of a piece of sheet was cut off from the sheet (harmful-insect-eliminating formed resin article) produced by press forming. The piece was divided into three square fragments whose sides had a length of about 3 mm. The fragments were weighed precisely together. The weighed fragments were put into acetone (about 50 ml) and the mixture was refluxed for two hours. The acetone solution after the reflux was analyzed by gas chromatography. From the results, the amounts (initial amounts) of the individual ingredients contained in a unit weight of press-formed sheet were determined.

On the other hand, the press formed sheet was aged in an oven (40° C.) for a predetermined period of time. A piece of sheet was cut off in the same manner as previously described from the sheet after the aging. By performing treatment and analysis the same as those described above, the amounts (residual amounts) of the individual ingredients contained in a unit weight of the sheet after the aging were determined. The ratio of a "residual amount" to an "initial amount" is the "residual ratio". The results obtained are shown in Table 2.

Conditions of gas chromatography are as follows:

Analyzer: GC-14A (manufactured by Shimadzu Corp.)

Column: Thermon 1000 (manufactured by Shinwa Chemical Industries, LTD.)

Column temperature: 145° C.

Carrier gas: $N_2$

Rate of carrier: 60 ml/min

Internal standard: Trimethylphosphate

Detector: FID

Comparative Example 1

A sheet was produced in the same manner as Example 1 except using an ethylene-methacrylic acid copolymer (available as CG4002 available from Sumitomo Chemical Co., Ltd.) in place of 1,2-polybutadiene. The residual ratios of the individual ingredients were determined. The results obtained are shown in Tables 1 and 2.

Example 2

A mixture was prepared by mixing 96.1% by weight of 1,2-polybutadiene (ditto) powdered by freeze grinding, 0.7% by weight of eucalyptol and 3.2% by weight of pulegone using a supermixer. By injection molding the resulting mixture, obtained was an animal collar (harmful-insect-eliminating formed resin article) 60 cm in length, 1 cm in width and 3 mm in thickness. The residual ratios of the harmful insect eliminators contained in the animal collar were determined according to the method described in Example 1. The results are shown in Table 3.

Comparative Example 2

An animal collar was produced in the same manner as Example 2 except using a polyvinyl chloride resin (available as ZEST1000S from SHIN DAIICHI ENBI) in place of a 1,2-polybutadiene. The residual ratios of the individual ingredients were determined. The hardness was measured in the same manner as Example 1.

The results obtained are shown in Tables 1, 2 and 3.

TABLE 1

| | Example 1 | | Comparative Example 1 | | Comparative Example 2 | |
|---|---|---|---|---|---|---|
| Ingredient | Content (%) | Ingredient | Content (%) | Ingredient | Content (%) |
| RB810 | 96.1 | CG4002 | 96.1 | PVC | 96.1 |
| Eucalyptol | 0.7 | Eucalyptol | 0.7 | Eucalyptol | 0.7 |
| Pulegone | 3.2 | Pulegone | 3.2 | Pulegone | 3.2 |
| Hardness | 70.5 | Hardness | 66.3 | Hardness | 71.7 |

RB810: Polybutadiene available from JSR Corp.
CG4002: Ethylene-methacrylic acid copolymer available from Sumitomo Chemical Co., Ltd.
PVC: Polyvinyl chloride

TABLE 2

| Volatile harmful-insect-eliminating component Elapsed time (day) | Eucalyptol | | | Volatile harmful-insect-eliminating component Elapsed time (day) | Pulegone | | |
|---|---|---|---|---|---|---|---|
| | Example 1 Residual ratio (%) | Comparative Example 1 Residual ratio (%) | Comparative Example 2 Residual ratio (%) | | Example 1 Residual ratio (%) | Comparative Example 1 Residual ratio (%) | Comparative Example 2 Residual ratio (%) |
| 0 | 100 | 100 | 100 | 0 | 100 | 100 | 100 |
| 5 | 62.5 | — | — | 5 | 38.2 | — | — |
| 8 | 48.9 | — | 41 | 8 | 28.4 | — | 36 |
| 14 | — | 4.3 | — | 14 | — | 1.3 | — |
| 15 | — | — | 30 | 15 | — | — | 20 |
| 18 | 37.5 | — | — | 18 | 10.6 | — | — |

TABLE 3

| Volatile harmful-insect-eliminating component Elapsed time (day) | Eucalyptol | | Volatile harmful-insect-eliminating component Elapsed time (day) | Pulegone | |
|---|---|---|---|---|---|
| | Example 2 Residual ratio (%) | Comparative Example 2 Residual ratio (%) | | Example 2 Residual ratio (%) | Comparative Example 2 Residual ratio (%) |
| 0 | 100 | 100 | 0 | 100 | 100 |
| 7 | 63.5 | — | 7 | 32.1 | — |
| 8 | — | 41 | 8 | — | 36 |
| 14 | 56.8 | — | 14 | 22.5 | — |
| 15 | — | 30 | 15 | — | 20 |

As is clear from the above results, the harmful-insect-eliminating formed resin article containing 1,2-polybutadiene and a volatile harmful-insect-eliminating component (harmful-insect-eliminating formed resin article of the present invention has a hardness (flexibility) the same as that of formed articles using a polyvinyl chloride resin as a base resin. In addition, it is also clear that the harmful-insect-eliminating formed resin article can cause much controlled volatilization of a volatile harmful-insect-eliminating component than that caused by formed articles using a polyolefin resin having a polar group as a base resin and therefore the formed article can exhibit an efficacy in eliminating harmful insects for a long period of time.

As described above, the harmful-insect-eliminating formed resin article of the present invention contains a 1,2-polybutadiene resin and a volatile harmful-insect-eliminating component.

As a result, it has a flexibility the same as that of formed articles using a polyvinyl chloride resin as a base resin. Furthermore, since a 1,2-polybutadiene resin gives less bad effect to the environment, the harmful-insect-eliminating formed resin article of the present invention can be used preferably. Moreover, since the harmful-insect-eliminating formed resin article of the present invention uses a 1,2-polybutadiene resin as a base resin, it causes much controlled volatilization of a volatile harmful-insect-eliminating component than that caused by formed articles using a polyolefin resin having a polar group as a base resin. Therefore, it can exhibit an efficacy in eliminating harmful insects for a long period of time. Accordingly, it can suitably be used in applications such as animal collars.

In the harmful-insect-eliminating formed resin article of the present invention, it is preferable that the volatile harmful-insect-eliminating component be at least one substance selected from eucalyptol and pulegone.

When a 1,2-polybutadiene resin is used as a base resin constituting a harmful-insect-eliminating formed resin article and at least one substance selected from eucalyptol and pulegone as a volatile harmful-insect-eliminating component, it is easy to produce a formed article and an effect in which an efficacy in harmful insect elimination against flea is held for a long period of time.

In the harmful-insect-eliminating formed resin article of the present invention, it is preferable that monomer units polymerized through a 1,2-addition reaction be contained in an amount of not less than 90% of the whole monomer units constituting the 1,2-polybutadiene resin.

In the harmful-insect-eliminating formed resin article of the present invention, it is preferable that the tacticity of the 1,2-polybutadiene resin be syndiotactic.

The harmful-insect-eliminating formed resin article of the present invention preferably has a hardness, as measured with a type A durometer according to JIS K6253, within the range of from 60 to 77.

The harmful-insect-eliminating formed resin article of the present invention is preferably used as an animal collar.

The animal collar of the present invention comprises any of the above-described harmful-insect-eliminating formed resin articles.

Since the animal collar comprises a harmful-insect-eliminating formed resin article containing a 1,2-polybutadiene resin and a volatile harmful-insect-eliminating component, it gives less bad effect to the environment, is superior in flexibility, and can exhibit an efficacy in eliminating harmful insects for a long period of time.

What is claimed is:

1. A harmful-insect-eliminating formed resin article, wherein the article contains a 1,2-polybutadiene resin and a volatile harmful-insect-eliminating component in an amount effective for eliminating a harmful insect,
    the volatile harmful-insect-eliminating component is at least one substance selected from the group consisting of eucalyptol and pulegone;
    the 1,2-polybutadiene resin is a homopolymer of butadiene; and
    the 1,2-polybutadiene resin contains monomer units polymerized through a 1,2-addition reaction in an amount of not less than 90% of the whole monomer units constituting the 1,2-polybutadiene resin.

2. The harmful-insect-eliminating formed resin article according to claim 1, wherein the article has a hardness, as measured with a type A durometer according to JIS K6253, within the range of from 60-77.

3. An animal collar comprising the harmful-insect-eliminating formed resin article according to claim 1.

4. The harmful-insect-eliminating formed resin article according to claim 1, wherein the tacticity of the 1,2-polybutadiene resin is syndiotactic.

5. The harmful-insect-eliminating formed resin article according to claim 1, wherein the article has a hardness, as measured with a type A durometer according to JIS K6253, within the range of from 60-77.

6. An animal collar comprising the harmful-insect-eliminating formed resin article according to claim 1.

7. The harmful-insect-eliminating formed resin article according to claim 4, wherein the article has a hardness, as measured with a type A durometer according to JIS K6253, within the range of from 60-77.

8. An animal collar comprising the harmful-insect-eliminating formed resin article according to claim 4.

9. An animal collar comprising the harmful-insect-eliminating formed resin article according to claim 5.

* * * * *